United States Patent [19]

Kern et al.

[11] Patent Number: 4,457,756
[45] Date of Patent: Jul. 3, 1984

[54] NOSE BLEED CLIP

[76] Inventors: Eugene B. Kern, 1708 Viola Rd., NE.; William B. Westwood, 211 SW. 23 Ave., both of Rochester, Minn. 55901

[21] Appl. No.: 368,317

[22] Filed: Apr. 14, 1982

[51] Int. Cl.³ .................... A61B 17/24; A61M 31/00
[52] U.S. Cl. ........................................ 604/286; 604/1; 604/890; 128/325; 128/342; 128/354
[58] Field of Search ................................ 128/325–326, 128/346, 342, 354; 604/1–3, 890, 285–286

[56] References Cited

U.S. PATENT DOCUMENTS

| | | | |
|---|---|---|---|
| 820,948 | 5/1906 | Baum | 604/285 X |
| 2,757,665 | 8/1956 | Tanikawa | 128/346 X |
| 3,342,183 | 9/1967 | Edenbaum | 128/325 X |
| 3,349,771 | 10/1967 | Baer | 128/325 |
| 4,369,783 | 1/1983 | Hiller et al. | 604/890 X |
| 4,378,802 | 4/1983 | Ersek | 128/346 |

FOREIGN PATENT DOCUMENTS 227,518  8/1967  U.S.S.R. ............... 128/346

*Primary Examiner*—Dalton L. Truluck
*Attorney, Agent, or Firm*—Herman J. Hohauser

[57] ABSTRACT

A device for treatment of nose bleed, the invention in a preferred embodiment takes the form of a bifurcated clip having opposed legs connected by a bight portion to gently urge the distal ends of the legs toward each other. The distal end of each leg is provided with an absorbent pad substantially saturated with a vasoconstrictive agent, the ends of the clip and thus the medicated pads disposed on the clip ends being slipped into the nose in the event of nose bleed. The pads contact those portions of the nasal mucosa lying on the septum immediately inside of the nostrils, common nose bleed typically occurring from these portions of the nasal mucosa. A stop element disposed on at least one of the legs prevents insertion of the clip ends beyond a safe distance into the nasal cavity. The action of the vasoconstrictive agent on the mucosa as well as the gentle pressure exerted by the clip itself acts to control bleeding. The pressure exerted by the clip can further be augmented by finger pressure on external portions of the clip or on the external surfaces of the tip of the nose.

10 Claims, 8 Drawing Figures

NOSE BLEED CLIP

BACKGROUND OF THE INVENTION

1. Field of the Invention

The present invention relates generally to apparatus for treating common nose bleed and particularly to disposable devices usable without prior training in first aid situations for controlling simple bleeding from the nasal mucosa.

2. Description of the Prior Art

Since nose bleed is almost universally suffered, it is not surprising that non-medical "home" remedies typically employed to treat this condition take a variety of colorful and typically ineffective forms. Even though nose bleed is not usually severe enough to warrant medical attention, no simple and convenient standard method has previously existed for controlling "nose bleed" in the typical first aid situation. Typical home remedies for simple nose bleed include the tilting back of the head, application of cold compresses to the neck, forehead or other areas about the nose, or manual attempts to compress the nostrils to control the flow of blood. Such techniques ordinarily used by non-medical laymen are not readily effective since action is typically not directed to the actual site of bleeding from within the nasal cavity. In "simple" or "common" nose bleed, the actual bleeding site corresponds to the location of a vascular plexus comprising a network of minute blood vessels and capillaries on the midline nasal partition or nasal septum. This vascular complex of the internal nose converges on an area on the front part of the nasal septum and lies approximately within an inch inside of the nose as measured from the nostril. Approximately 90 percent of all nose bleeds occur within this region. This anatomically significant vascular plexus is commonly referred to as the Kiesselbach's Area or plexus and it is from this vascular confluence that the great majority of nose bleeds originate. While more complicated profuse or severe nose bleed can and should be managed by trained medical personnel through the use of specialized equipment and techniques such as nasal packing, no quickly effective, reliable methodology or instrument exists for the treatment of common nose bleed by the medically untrained layman since present first aid measures and home remedies do not reach the source of bleeding internally of the nose as referred to above.

In spite of the general lack of efficacy associated with prior home or first aid treatment for nose bleed, there has been no lack of effort and imagination in prior attempts to deal with the problem. A patented example of a simple prior device intended for controlling nasal hemorrhage is disclosed by Baer in U.S. Pat. No. 3,349,771, this patent describing a nasal clamp having legs which are spread apart and placed over exterior portions of the nostrils in an effort to exert pressure on the nose. While the clamp of Baer is simple in construction and operation, the Baer device does not act in the manner of the present invention to exert force directly upon the mucosa from which common nose bleed typically originates.

Surgical packs and similar nasal hemostats are described in a number of prior patents, these prior devices requiring use by experienced medical personnel. As examples, Stevens in U.S. Pat. No. 2,179,964; McMillan in U.S. Pat. No. 2,215,126; Fortay in U.S. Pat. No. 3,420,237; and Kriwkowitsch in U.S. Pat. No. 3,049,125 describe nose packs and methodology for treating severe epistaxis. Kriwkowitsch in particular describes an inflatable body adapted to be expanded into the nasal cavity for control of severe nasal hemorrhage, the device including a manometer bulb for inflation of the balloon-like body for maintaining pressure against a bleeding vessel. Gottschalk in U.S. Pat. No. 3,850,176, describes a self-retaining nasal tampon intended for controlling nasal hemorrhage and also including inflatable members for exerting pressure against hemorrhaging nasal vessels. Walker in U.S. Pat. No. 3,884,241 provides a foam rubber packing used to control bleeding from posterior portions of the nasal cavity and further provides for administration of nasal anesthesia. In U.S. Pat. No. 4,030,504, Doyle provides an expandable elongated hemostat for application of pressure to portions of the nasal cavity. While these prior devices provide useful treatment modalities for severe nose bleed when administered by medically trained personnel, the art has failed to provide a safe, simple and reliable means which is simple in use, inexpensive and effective in controlling nose bleed, and which can be used even by the patient himself without prior training.

Mention is also to be made of U.S. Pat. No. 576,441 to Farmer and U.S. Pat. No. 2,757,665 to Tanikawa. Farmer describes a nasal expander which utilizes suction cups disposed at the end of a U-shaped clip, the cups acting to adhere to the nose and to force the nostrils to spread apart to improve breathing. While the Farmer device superficially resembles at least one embodiment of the present invention, the Farmer patent is clearly not useful in the manner of the present invention and is not intended to control nose bleed. Tanikawa also provides a mechanical device which superficially resembles at least one embodiment of the present invention. However, the Tanikawa device is intended to shape the human nose and is not used in the manner of the present invention nor can it be so used for the purpose of treating nose bleed.

The present invention provides for the first time a simple, inexpensive and effective device for controlling nose bleed, the device being sufficiently inexpensive that it can be configured for disposable use. Further, the devices configured according to the present invention can be utilized by individuals lacking medical training. It can even be safely and effectively used by the person himself (herself) suffering from the nose bleed.

SUMMARY OF THE INVENTION

The present invention provides in several embodiments devices for controlling those common forms of nose bleed which do not require medical attention. In particular, the present devices can be utilized by untrained individuals for the majority of the simple nose bleeds encountered in daily situations and which typically involve minor direct nasal injury from a blow to the nose, colds, respiratory infections, low humidity, sneezing, nasal drug abuse, hypertension, persons using a variety of blood thinners, and the picking of the nose as well as those forms of sudden, unexplained and spontaneous nose bleed. These various causes for nose bleed represent over 70 percent of the various forms of nose bleed. The preferred embodiment of the present device particularly provides two absorbent pad elements moistened with a non-prescription vasoconstrictive agent, the pads being carried by a spring-like clip which acts to maintain the medicinally treated pad in contact with that portion of the nasal mucosa on the midline nasal septum from which the overwhelming majority of nose bleeds originate. It is understood that if desired only one absorbent pad may be used. The present clips are configured to safely and painlessly reach and contact this portion of the nasal mucosa lying approximately three-quarter inch to one inch inside the nose on the nasal septum. This area being a vascular plexus known as the Kiesselbach's Area and comprising a confluence of minute vessels lying near the surface of the nasal mucosa at the front of the nose. The present devices find primary effectiveness by virtue of the fact that a vasoconstrictive agent is applied directly to the site of the nose bleed with pressure being applied to this site by means of gentle spring-like action exerted by the devices without the requirement for externally applied prssure. However, the pressure exerted by the present devices can be augmented by finger pressure applied to external portions of the devices or the external surfaces of the tip of the nose.

A first embodiment of the invention can be described as a flexible, compression clip comprised of longitudinally extending, substantially parallel leg portions joined at one end of the device by means of a bight portion. The material from which the device is formed is chosen to have a certain degree of elasticity such that the free ends of the legs tend to resume their original configuration after biasing of the free ends apart. The free end of each leg is provided with an absorbent pad formed of a material such as cotton and which is capable of absorbing and retaining a vasoconstrictive agent such as phenylephrine hydrochloride, a non-prescription topical vasoconstrictive agent typically used as an aqueous solution. In the event of nose bleed the free ends of the clip are inserted into the nostrils and are thus caused to bias gently inwardly toward the nasal septum to contact the vascular plexus of the nasal mucosa from which nose bleed commonly originates. A stop positioned on at least one of the legs prevents insertion of the legs of the clip beyond the desired region of nose bleed origin. The natural spring-like action of the clip, whether or not augmented by external finger pressure, causes the padded free ends of the clip to move toward each other and compress the nasal septum and thus exert gentle pressure sufficient to constrict the blood vessels and thereby control bleeding from the most common site of common anterior nose bleed.

In a similar fashion, devices can be configured according to the present invention with an absorbent pad disposed on the free end of one leg of a U-shaped clip while the free end of the other leg is provided with a smooth bulbous free end portion which is inserted into that nostril from which bleeding is not originating. Such a modification is primarily useful for those situations wherein bleeding is occurring from only one side of the nasal septum. Clip-like devices according to the invention can also be configured with one leg bearing an absorbent pad carrying a vasoconstrictive agent and with a second opposing leg which contact external surfaces of the nose, or, in other embodiments, the interior of a nostril on the outward side thereof, such a device thus having both legs extending into the same nostril with the padded leg contacting the surface of the nasal septum. In further embodiments, either the body of the clip or the free ends of the clip can be formed of an absorbent material so as to make that structure corresponding to the absorbent pads integral with the body of the clip or with the legs of the clip. In still further embodiments, stops which limit penetration of the free ends of the clips can be provided through the use of enlarged shoulders disposed adjacent to the absorbent pads or by configuring the clip such that the legs are of a length sufficient only to reach the region of the nasal mucosa from which the majority of common nose bleeds originate as described above. Yet another embodiment of the clip can be so structured that it can be inserted, squeezed and withdrawn with the use of one hand.

Accordingly, it is a primary object of the present invention to provide devices for treatment of simple nose bleed, the devices being provided with absorbent elements capable of absorbing and retaining a vasoconstrictive agent, the vasoconstrictive agent being brought into contact with an appropriate portion of the nasal mucosa by contact between at least one of the absorbent elements and the nasal mucosa.

It is another object of the invention to provide simple, inexpensive and effective disposable devices which enable an untrained layman to treat simple nose bleed, the devices having a natural spring-like action for exerting pressure against the nasal mucosa when inserted into the nostrils.

It is a further object of the present invention to provide simple reliable devices which can be used by an untrained layman either on himself or on another with minimum instructions as to the effective use of the devices, the devices being of a size and cost which allows ready and common provision thereof in first aid kits and medicine cabinets so that the devices will be readily available for immediate treatment of an individual suffering from nose bleed and before a significant quantity of blood is lost.

It is yet another object of the present invention to provide devices for controlling simple nose bleed wherein the devices can be configured in sizes adequate for use in children and adults and which can be packaged in air-tight foil packets with absorbent pads disposed on the devices being pre-soaked in a suitable vasoconstrictive agent, the devices thus being thereby maintained in an antiseptically clean environment and kept readily available for emergency use.

Further objects and advantages of the invention will become more readily apparent in light of the following detailed description of the preferred embodiments.

DESCRIPTION OF THE PREFERRED EMBODIMENTS

Figure 1:
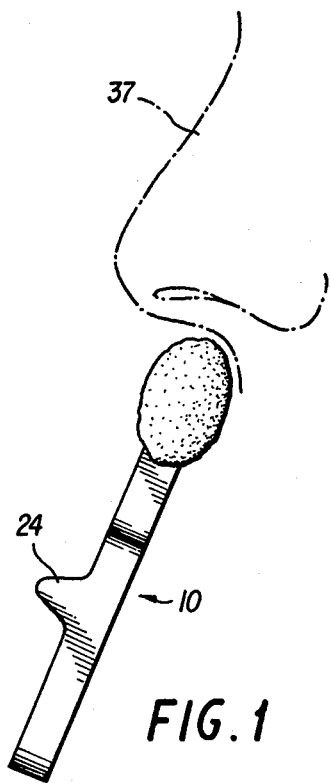
FIG. 1 is a side elevational view of a first embodiment of the nose bleed clip shown immediately prior to insertion of the free ends thereof into the nasal cavities of the nose.

Referring now to the drawings and particularly to FIGS. 1 through 4, a first embodiment of the invention is seen at 10 to comprise a clip 10 shaped generally in the manner of a hairpin, that is, the body of the clip 10 is formed in a generally U-shaped configuration. The clip 10 is comprised of a pair of legs 12 and 14 which are elongated and extend in substantially parallel relation to each other, the legs being joined at one set of adjacent ends by a bight portion 16. The distal or free ends of the legs 12 and 14 respectively carry absorbent pads 18 and 20 as will be described in more detail hereinafter. Stop elements 22 and 24 are respectively disposed on the legs 12 and 14 intermediate the ends of said legs 12 and 14, the stop elements acting to limit the depth to which said legs may be inserted into the nostrils.

Those portions 26 and 28 of the respective legs 12 and 14 adjacent the bight portions 16 are preferably spaced apart from each other by a greater distance than are the end portions 30 and 32, the end portions 30 and 32 being connected to the portions 26 and 28 respectively by laterally recurved shoulders 34 and 36. The end portions 30 and 32 are preferably separated from each other by a smaller distance than are the portions 26 and 28 so that the clip 10 in a normal unstressed position will have the absorbent pads 18 and 20 lying in juxtaposition to each other while the portions 26 and 28 form a sufficiently large structure to facilitate handling of the clip 10.

The body of the clip 10 is typically formed of either metal, plastic or a combination thereof, and the particular material chosen is selected for a desired stiffness and elasticity such that deformation of the legs 12 and 14 outwardly results in tension being exerted by the body of the clip 10 to close the end portions 30 and 32 back together on release of the deforming force. The material from which the body of clip 10 is formed is further chosen and constructed so as not to irritate or have any otherwise adverse effect upon the skin or nasal mucosa. The inward deformation of end portions 30 and 32 allow clip to function without hitting or binding on the nasal columella.

Figure 4:
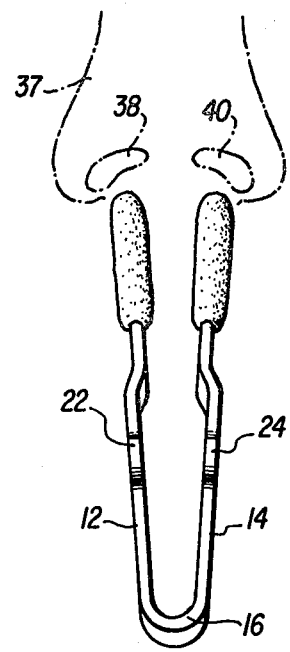
FIG. 4 is a perspective view of the first embodiment of the present nose bleed clip shown in an idealized used environment wherein the legs of the clip are biased outwardly for insertion into a nose as shown in phantom.

The clip 10 is preferably packaged in air-tight foil packet such as is standardly used to package articles which are pre-soaked or otherwise contacted with a given chemical substance. Such a pre-packaged device can be kept in the home in the medicine cabinet, in first aid kits, in school and other first aid stations and the like for immediate use in the event of simple nose bleed emergency. When such a nose bleed does occur, the packet can be readily opened and the clip 10 slipped into the nose such as is generally indicated in FIGS. 1 and 4, the end portions 30 and 32 being biased outwardly of each other to allow reception of the absorbent pads 18 and 20 one each into each of the nostrils. Once the absorbent pads 18 and 20 are suitably disposed within the nostrils, the force deforming the legs 12 and 14 outwardly, such force typically being exerted by the fingers, is discontinued and the absorbent pads 18 and 20 allowed to contact the nasal mucosa internally of the respective nostrils. The stop elements 22 and 24 facilitate insertion of the absorbent pads 18 and 20 into the nostrils by allowing a user to gauge the proper depth of insertion and to prevent the legs 12 and 14 of the clip 10 from being inserted too great a distance into the nose. The general pressure naturally exerted by the end portions 30 and 32 of the clip 10 against the nasal mucosa, in concert with the action of a vasoconstrictive agent absorbed on the pads 18 and 20, causes constriction of the minute blood vessels and capillaries within the nasal mucosa to thus cause cessation of bleeding. It is to be understood that the stop elements 22 and 24 can be otherwise configured, such as by enlargement of one or more of the shoulders 34 and 36. Further, only one stop element on one of the legs 12 or 14 could be utilized to properly gauge the necessary insertion of the clip 10 into the nose. It is also to be understood that legs 12 and 14, which are typically of the same length, can also be spaced apart by a given distance along their full lengths, such a distance being necessarily of a degree such that the legs 12 and 14 cause the absorbent pads 20 and 22 to lie substantially in adjacent and contiguous relation to each other when in a nonstressed conformation.

Figure 3:
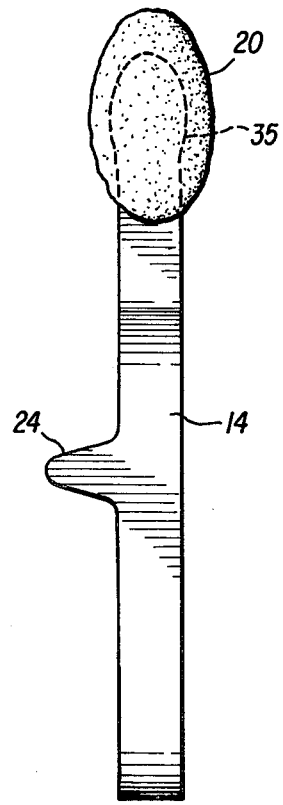
FIG. 3 is a side elevational view of the first embodiment of the present nose bleed clip.

As can best be seen in FIG. 3, the free ends of the legs 12 and 14 distally of the end portions 30 and 32 are enlarged so as to provide a more suitable seating for the absorbent pads 18 and 20. The enlarged heads 35 facilitate mounting of the absorbent pads 18 and 20 to the distal ends of the legs 12 and 14 and thus reduce the possibility of accidental dislodgement of the pads from the ends of the legs. The enlarged area of the heads 35 further acts to increase the area over which pressure is exerted against the nasal mucosa.

Figure 2:
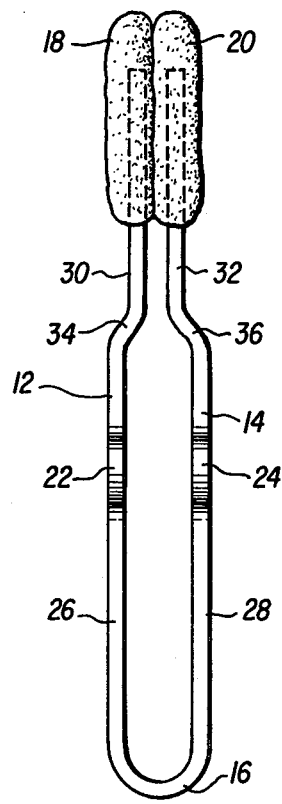
FIG. 2 is a front elevational view of the first embodiment of the present nose bleed clip.

While the clip 10 could be used without provision of a topical vasoconstrictive agent absorbed into the pads 18 and 20, the structure functions best when such a coagulant agent is used since both the constrictive effects of the agent and the effects of pressure inherently applied by virtue of the structure of the clip 10 is brought to bear upon that portion of the nasal mucosa from which the nose bleed originates. The absorbent pads 18 and 20 are typically formed of cotton or similar absorbent material which is also resilient within the sense that a textile material is resilient, thereby facilitating the adherence of the pads 18 and 20 to the ends of the legs 12 and 14 and further allowing ready absorption of the vasoconstrictive agent into the pads. Since the pads 18 and 20 normally engage each other when the clip is in an unstressed configuration such as is shown in FIG. 2, the vasoconstrictive agent held in the pads will typically be spread evenly over the contiguous innermost surfaces of said pads. The tendency for the vasoconstrictive agent to evaporate is thus reduced to a certain degree due to the diminution of pad surface area exposed to the ambient environment. As seen in relation to FIG. 2, the total exposed surface area of the pads 18 and 20 when in the unstressed configuration is only slightly more than the total surface area of a single pad.

As seen particularly in FIGS. 2 and 3, the absorbent pads 18 and 20 act to completely cover the distal ends of the legs 12 and 14 including the enlarged heads 35 thereof. The heads 35 are further seen to be formed to be free of sharp corners and with blunt edges to prevent the accidental scratching of any part of the nasal mucosa on insertion of the clip 10 into nostrils 38 and 40 of the nose 37.

The clip 10 of FIGS. 1 through 4 is readily seen to be particularly useful in situations where bleeding may be originating from both nostrils, the clip 10 being positioned relative to the nose 37 as seen in FIG. 4 to allow both of the pads 18 and 20 to be inserted into the nostrils 38 and 40 for contact of the pads with the surfaces of the nasal mucosa on the nasal septum internally of both nostrils. The absorbent pads 18 and 20 containing the vasoconstrictive agent are thus caused to lie over those portions of the nasal mucosa from which simple nose bleed commonly originates. That portion of the nasal mucosa which is bleeding can also be contacted by one of the pads 18 or 20 even though the legs 12 and 14 may be inserted to a depth lesser than that provided by the stop elements 22 and 24 in the event that bleeding is originating from a site closer to the nasal openings. The stop elements 22 and 24 are further formed with blunt edges and are free of sharp corners which could act to scratch the lower ends of the nostrils 38 and 40.

After the clip 10 is properly positioned in a use situation, the legs 12 and 14 are released, the clip then acting due to its inherent resiliency to apply at least some of the pressure needed to constrict the blood vessels within the nasal mucosa in order to stop bleeding from the mucosa. The structure of the legs 12 and 14 allow the clip 10 to close on the nasal septum without interference from the lower part of the septum. Since the absorbent pads 18 and 20 preferably contain a topical vasoconstrictive agent, the pressure required to stop blood flow is somewhat less than would ordinarily be necessary. Finger pressure to the external tip of the nose can be used such as by touching the nostrils either by the patient or by an attendant to augment the pressure exerted by the clip itself. In use, a user of the clip 10 experiences little or no discomfort when the clip is applied to the nose.

While in a preferred embodiment the absorbent pads 18 and 20 typically are formed of a cotton batting and the body of the clip 10 is formed of a resilient polypropylene plastic, other materials can easily by utilized. Further, while a number of well known vasoconstrictive agents can be employed, it is preferred to use phenylephrine, a well known vasoconstrictive agent which is disclosed in U.S. Pat. Nos. 1,932,347 and 1,954,389, this material being safe and effective to provide the necessary vasoconstrictive results and approved for this function by the U.S. Federal Drug Administration. In use, the pads 18 and 20 will each advantageously contain approximately two milliliters of phenylephrine, usually used as a one percent solution for adults, a 0.5 percent solution for children four to twelve years old and a 0.25 percent solution for children between two and four years of age. The clip 10 described relative to FIGS. 1 through 4 conveniently is configured to be approximately seven centimeters long and approximately 0.2 centimeters in width with the stop elements 22 and 24 being located along the legs 12 and 14 at a distance of approximately four centimeters from the inner ends of the pads 18 and 20. The pads 18 and 20 are approximately two centimeters long, 1.5 centimeters high and 0.3 centimeters wide.

Figure 5:
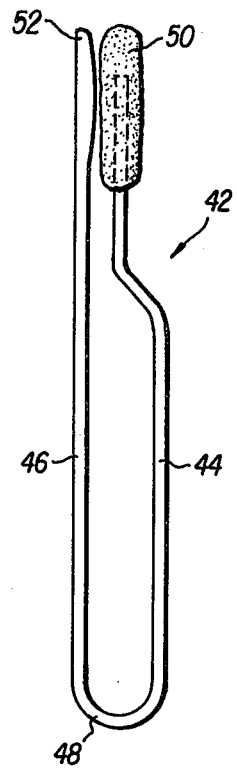
FIG. 5 is a side elevational view of a second embodiment of the invention.

Referring now to FIG. 5, a clip 42 is seen to be configured substantially identically to the clip 10 with legs 44 and 46 connected by a bight portion 48. However, in this embodiment, only one of the legs is provided with an absorbent pad 50 while the other leg is provided with a slightly enlarged and rounded distal end portion 52. The clip 42 is thus useful in those situations where bleeding occurs from only one nostril. The clip 42 is used in essentially the same manner as is the clip 10 except that the absorbent pad 50, which is physically saturated with a vasoconstrictive agent, is inserted into the nostril in which bleeding is occurring while the end portion 52 is inserted into the other nostril. The rounded end portion 52 biases against one side of the nasal septum while the absorbent pad 50 biases against the other side of the nasal septum to produce essentially the same result as is produced by the clip 10. Through use of the clip 42, a somewhat less expensive device can be produced. It is understood that stops such as stop 24 shown in FIGS. 1 and 3 may be provided on clip 42.

Figure 6:
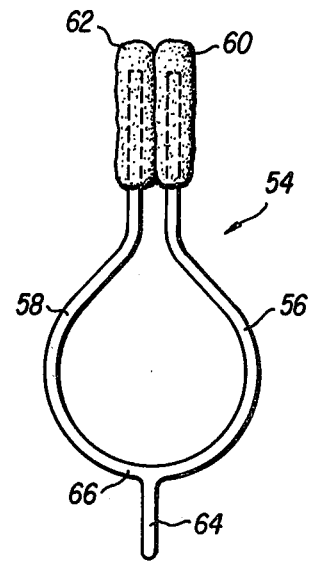
FIG. 6 is a side elevational view of a third embodiment of the invention.

As seen in FIG. 6, a clip 54 is provided having legs 56 and 58 which are themselves of a length equal to the maximum depth to which the clip 54 would be inserted into the nose. In this embodiment, absorbent pads such as the pads 60 and 62 would be carried on at least one of the legs, the clip 54 being used in an identical manner as is the clip 10 with the exception that only a minor portion of the body of the clip 54 extends externally of the nose when the clip 54 is in use. A tab 64 can be provided on bight portion 66 of the clip 54 to enable ready handling of the clip 54. The legs 56 and 58 as well as the bight portion 66 of the clip 54 are formed arcuately as shown in FIG. 6 with the legs 56 and 58 not being parallel but being spaced apart at the greatest distance near most the bight portion 66 and curving toward each other such that the legs 56 and 58 are near most at their distal end portions. In use, the clip 54 can be grasped by means of the tab 64 as well as at the widely spaced apart portions of the legs 56 and 58 near the bight portion 66 to facilitate "opening" of the clip 54 for insertion of the absorbent pads 60 and 62 into the nostrils. The clip 54 can then be inserted the full distance possible into the nose, engagement of the inner surfaces of the bight portion 66 with the septum of the nose preventing undue penetration of the legs 56 and 58 into the nostrils.

Figure 7:
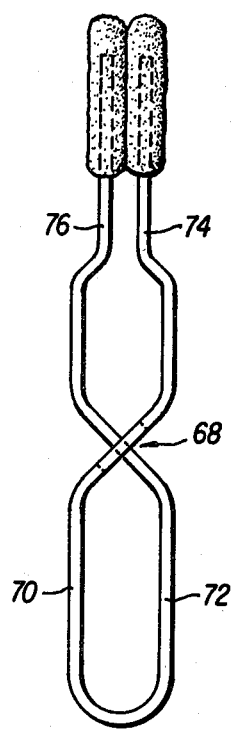
FIG. 7 is a side elevational view of a fourth embodiment of the invention.

Clip 68 shown in FIG. 7 is provided so that it can be inserted, squeezed, and withdrawn using one hand. As can be seen, if pressure is exerted on portions 70 and 72 as with a user's thumb and index finger, leg portions 74 and 76 will move away from each other for easy insertion or withdrawal from the nose.

Figure 8:
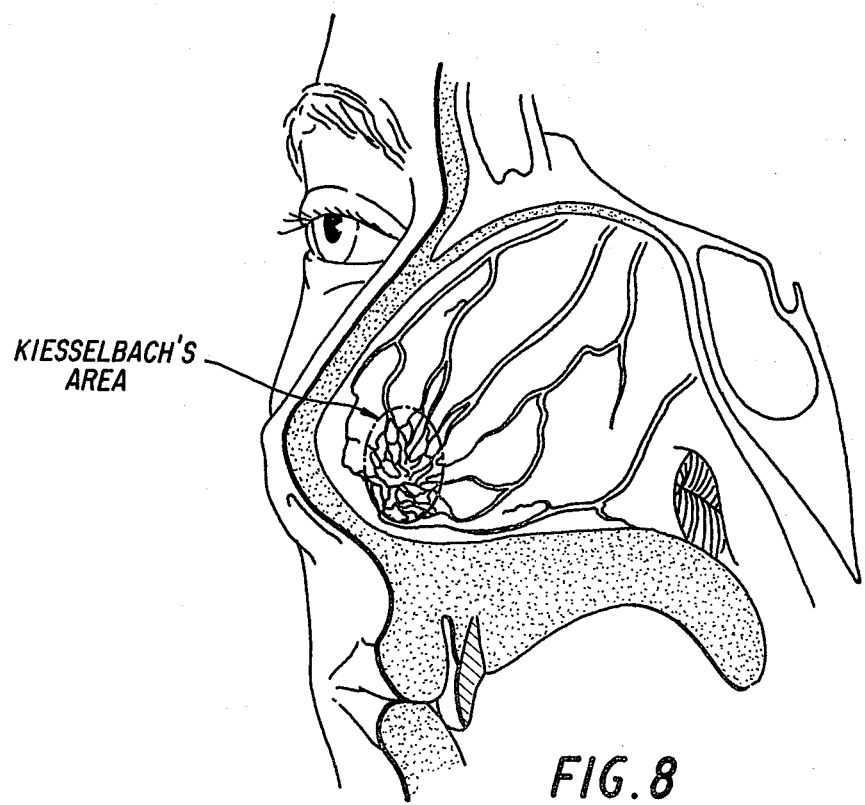
FIG. 8 is an idealized illustration of the human head with a section taken through the midline of the nasal partition to show the confluence of minute vessels constituting the vascular plexus from which the majority of simple nose bleeds originate.

Referring now to FIG. 8, an idealized view of the human nose illustrating the Kiesselbach's Area is shown, this area being that region of the nasal mucosa which is to be preferably contacted by the vasoconstrictive agent-containing absorbent pads of the various clips configured according to the invention. As indicated above, the great majority of simple nose bleeds occur from the Kiesselbach's Area and the application of a vasoconstrictive agent along with pressure exerted by the clips of the invention is typically adequate to stop bleeding which occurs from this region of the mucosa.

It is to be understood from a consideration of the foregoing description of the preferred embodiments, that the invention can be practiced other than is explicitly described hereinabove. Accordingly, it is not the intent of the foregoing specification to limit the invention to any particular embodiment or embodiments. It is the present intent to provide teachings which will lead to various embodiments of the invention as are contemplated according to the specification and as are defined as proprietary by the scope of the appended claims.

What is claimed is:

1. A device for treating nose bleed, comprising:
   a body element having a portion adapted to be received in one of the nostrils;

means carried by said body element for engaging a portion of the nose and for biasing said portion of the body element into engagement with a portion of the nasal mucosa to at least apply pressure to said portion of the nasal mucosa;

said body element being substantially U-shaped; said portion of the body element comprising a first elongated leg member; said means carried by said body element comprising a second leg member which biases against said portion of the nose to urge a portion of the first leg member into engagement with said portion of the nasal mucosa;

absorbent means disposed over the portion of the first leg member which engages said portion of the nasal mucosa;

said absorbent means being wetted with a vasoconstrictive agent;

wherein the vasoconstrictive agent comprises phenylephrine.

2. The device of claim 1 wherein the vasoconstrictive agent comprises a solution of phenylephrine in a concentration of 0.25 to 1.0 percent by weight of phenylephrine.

3. A device for treating nose bleed comprising:

a substantially U-shaped body element having a portion comprising a first elongated leg member adapted to be received in one of the nostrils;

a second leg member carried by said body element for biasing against a portion of the nose to urge a portion of said first leg member into engagement with a portion of the nasal mucosa with pressure;

said first leg member having an enlarged head portion on that portion of said first leg member which engages the nasal mucosa; and absorbent means disposed over said head portion.

4. The device of claim 3 wherein the absorbent means is wetted with a vasoconstrictive agent.

5. A device for applying pressure to the Kiesselbach's Area of the nasal mucosa to control simple nose bleed, comprising:

body means having spaced end portions for insertion of at least one end portion into one of the nostrils and for biasing the end portions toward each other; and means disposed on the end of at least one end portion which is inserted into said nostril for contracting the Kiesselbach's Area of the nasal mucosa, said means applying pressure to the nasal mucosa by virtue of the resiliency of the body means to control nose bleed originating in the vicinity of and in the Kiesselbach's Area;

wherein said body means is substantially U-shaped and comprises two elongated leg members extending at one end of said body means, the free ends of said leg members biasing against portions of the nasal mucosa thereof into the nostrils and absorbent means are disposed on the free ends of each of the leg members.

6. The device of claim 5 wherein the absorbent means comprise at least one pad formed of an absorbent material.

7. The device of claim 6 wherein the absorbent means is wetted with a vasoconstrictive agent.

8. A method for applying pressure and a vasoconstrictive agent to the Kiesselbach's Area of the nasal mucosa to control simple nose bleed, comprising the steps of:

providing a device having substantially parallel legs joined together at one end thereof and having an absorbent element disposed on the free end of at least one of the legs, the device having a natural spring-like bias urging the free ends of the legs toward each other;

wetting the absorbent element with the vasoconstrictive agent; and positioning the free ends of the legs over the Kiesselbach's Area of the nasal mucosa to apply pressure thereto at least by virtue of compressive force exerted by the device and to bring the vasoconstrictive agent into contact with the Kiesselbach's Area of at least one nostril.

9. The method of claim 8 and further comprising the step of applying pressure to that portion of the device extending externally of the nostrils to increase pressure on that portion of the nasal mucosa contacted by the device.

10. A device for treating nose bleed comprising:

a substantially U-shaped body element having a two elongated leg members extending substantially parallel to each other;

said leg members being joined by a bight portion at one end of said body element and having free ends at the other end of said body element; said body element having a natural spring-like bias urging said free ends toward each other; a projection formed on at least one of said leg members at a predetermined distance from said bight portion for stopping the insertion of the device in the nostril beyond a predetermined limit;

absorbent means disposed over the free end of at least one of said leg members;

a vasoconstrictive agent disposed on said absorbent means wherein the free end of said leg members can be inserted into a nostril to contact the Kiesselbach's Area of the nasal mucosa under pressure sufficient to stop the flow of blood originating in the vicinity of and in the Kiesselbach's Area.

* * * * *